US006105909A

United States Patent [19]

Wirth et al.

[11] Patent Number: 6,105,909

[45] Date of Patent: Aug. 22, 2000

[54] STAND WITH ENERGY STORAGE DEVICE FOR WEIGHT EQUALIZATION

[75] Inventors: Michael Wirth, Aalen; Dorothea Engelfried, Königsbronn; Christof Poglitsch, Aalen, all of Germany

[73] Assignee: Carl-Zeiss-Stiftung, Germany

[21] Appl. No.: 09/160,612

[22] Filed: Sep. 24, 1998

[30] Foreign Application Priority Data

Sep. 24, 1997 [DE] Germany ........................... 197 42 048
Sep. 24, 1997 [DE] Germany ........................... 197 42 049

[51] Int. Cl.$^{7}$ ........................................................ A47F 5/00

[52] U.S. Cl. .................................... 248/123.2; 248/125.2; 248/281; 248/11; 248/284.1; 359/384; 414/917

[58] Field of Search ........................... 248/123.2, 123.11, 248/125.2, 280.11, 281, 11, 292.11, 284.1; 359/384; 414/917

[56] References Cited

U.S. PATENT DOCUMENTS

| | | | |
|---|---|---|---|
| 4,339,100 | 7/1982 | Heller et al. | 248/123.1 |
| 4,685,648 | 8/1987 | Dobner et al. | 248/572 |
| 5,037,053 | 8/1991 | Fox et al. | 248/278 |
| 5,186,174 | 2/1993 | Schlondorff et al. | 128/653.1 |
| 5,242,142 | 9/1993 | Nakamura | 248/280.1 |
| 5,320,315 | 6/1994 | Kawamura et al. | 248/282 |
| 5,332,181 | 7/1994 | Schweizer et al. | 248/123.1 |
| 5,609,316 | 3/1997 | Tigiev | 248/123.11 |
| 5,667,186 | 9/1997 | Luber et al. | 248/550 |
| 5,746,404 | 5/1998 | Merko | 248/123.11 |
| 5,794,909 | 8/1998 | Platus et al. | 248/550 |
| 5,825,536 | 10/1998 | Yasunaga et al. | 359/384 |
| 5,855,844 | 1/1999 | Rogers | 248/123.2 |

FOREIGN PATENT DOCUMENTS

| | | |
|---|---|---|
| 0 433 426 B1 | 2/1994 | European Pat. Off. . |
| 221 571 A1 | 4/1985 | Germany . |
| 37 39 080 A1 | 5/1989 | Germany . |
| PCT/EP88/00457 | 5/1988 | WIPO . |

OTHER PUBLICATIONS

Gewichtassausgleich an feinmechanischen Geräten. Dipl.–Ing. H. Hilpert. Feingerätetechnik 14. Jg—Heft Feb. 1965.

*Primary Examiner*—Ramon O. Ramirez
*Assistant Examiner*—Walter Landry

[57] ABSTRACT

A stand for a device, which is to be movably arranged, has a first stand part and a second stand part, which is movable relative to the first stand part, and which includes a pivot arm, pivotable around a pivot axis (A2) and jointed to the first stand part. An energy storage device is provided, which exerts at a fixed point of action of the pivot arm a force directed to an abutment point of the energy storage device on the first stand part. The pivot axis (A2) and the abutment point define a vertical plane, the abutment point being spatially fixed relative to the first stand part during a pivoting of the pivot arm. A cord parallelogram coupling the motion of a first stand arm and a second stand arm includes a closed cord length running around two deflecting rollers, and has a rod section between the deflecting rollers. A linear slide and pivot unit is arranged between a mounting arm and the movably arranged device and makes possible displacements of the center of gravity of the movably arranged device.

33 Claims, 8 Drawing Sheets

80
A3
17

11
84
21
86
85
82
81
A6
23
81
9
83
A3'
19
22
24
A5
14
13
15
V
16
VIII
A4
3
IX
81
80
85
84
191
189
81
180
187
185

101
13
111
103
95
115
117
113
VII
VII
105
131
109
121
A5
125
99
119
127
107
123
129
15
14
97
98

101
13
111
103
115
113
117
105
131
109
125
A5
129
107
127
121
97
99
119
123
15
98

115
137
135
113
105
103
133
111
131
13

16
149

151
145
139
147
143
15
153
3
A4
141

156
149
145
157
161
147
145
A4
155
167
151
169
169

X 156
149
159
161
153
147
141
163
145
157
155
158
139
165
15
A4

201
33
11
23
25
A3
17
21
A6
35
27
19
A3'
245
9
246
47
13
22
249
24
248
A5
37
29
14
43
A2
15
16
41
50
44
39
3
A4
31
7
37
5
4
A1
4

245
249
248
47
250
253
251
265
9
257
246
248
263
255
261
259
7
A2

STAND WITH ENERGY STORAGE DEVICE FOR WEIGHT EQUALIZATION

BACKGROUND OF THE INVENTION

This invention relates to a stand for a movably arranged equipment, and more particularly to such a stand that has an energy storage device which is to compensate the torque of a useful load arranged on the pivot arm of the stand.

FIELD OF THE INVENTION

A stand of this kind is known from German Patent DE 37 39 080 A1.

Here the energy storage device includes a cord linked to a point of action on the pivot arm and deflected toward a tension spring by a deflecting roller arranged above the pivot axis. The energy storage device thus exerts a force at the point of action on the pivot arm, directed to that point of the circumference of the deflecting roller at which the straight cord section coming from the point of action contacts the deflecting roller circumference.

This contact point, denoted as an abutment point, travels on the deflecting roller circumference in dependence on the pivoted position of the pivot arm, since the deflecting roller has a diameter which is not equal to zero. Thus only an approximate, not an exact, weight equalization can be achieved with this stand.

The theory of such stands is also to be found in the article by H. Hilpert in FEINGERÄTETECHNIK, 14th year, Vol. 2/1965, entitled "Weight Equalization in Precision Mechanical Equipment" (see FIG. 7 on page 63 of this article). In this article by H. Hilpert, it is stated in the first paragraph of the left-hand column of page 63 that in the known stand, as a consequence of the finite curvature of the deflecting roller, that is, due to the displacement of the abutment point or due to an additional winding up or unwinding of the cord on pivoting of the pivot arm, only an approximate weight equalization can be achieved. Accordingly, the weight G acting on the pivot arm at a load distance l from the pivot axis is equalized when the condition is fulfilled that:

$$c' \cdot r' L = G \cdot l,$$

where c' is the spring constant of the weight equalization spring, r' is the vertical distance of the deflecting device from the pivot axis, and L is the distance of the point of action of the weight equalization force from the pivot axis.

This condition of course only leads to an exact weight equalization under the assumption of a point deflection, i.e., when the deflecting radius is equal to zero. This fact is also explicitly mentioned in the first paragraph of the left-hand column of page 63 of the article by H. Hilpert.

A stand of the category concerned is also known from East German Patent DD 221 571 A1, and is constructed on the principles in the article by H. Hilpert. However, the abutment point also travels in this stand in dependence on the respective position of the pivot arm, since the deflecting element, which deflects the cord connecting a tension spring to the pivot arm, is formed by an inclined surface with a finite curvature.

A further stand of the category concerned is known from U.S. Pat. No. 5,320,315, and includes a first stand arm, and a second stand arm which is rotatable relative to the first stand arm. In this known stand, a closed cord length or endless belt runs around a first deflecting roller which is rotatable relative to the first stand arm, and a second deflecting roller which is non-rotatably connected to the second stand arm. The motion of the first stand arm can thus be coupled to the motion of the second stand arm. In this stand, the first deflecting roller is fixed non-rotatably with respect to a stand base part, so that the second stand arm moves, when the first stand arm pivots, such that the orientation of the second stand arm remains constant relative to the stand base part Such a stand is also known from International Patent Publication WO 88/09151, in which several closed cord lengths constructed as endless belts are interconnected in series in order to couple the motion of one stand arm to the motion of equalizing weights. Thus this stand is brought into a weight equalizing state in each position of the stand arm.

However, the extensibility of a cord or belt or toothed belt leads to slip and delays in the coupling of the motion of the first and second stand arms.

A further stand of the category concerned is known from European Patent Document EP 0 433 426 B1. This stand carries an operation microscope, and has an adjusting device arranged between a mounting arm of the stand and the operation microscope, by means of which device the operation microscope is adjustable relative to the mounting arm. The center of gravity of the operation microscope can thus be displaced relative to the stand, in order to balance the system of the stand and the operation microscope.

In such a stand, a weight equalization is namely effected, i.e., the stand is balanced with regard to its rotational and pivoting axes, or the weight of the respective moving stand component and of the equipment suspended on the stand is equalized, in that on moving the equipment only the inertia of the two masses, and not weight forces, has to be overcome.

In this stand known from European patent Document EP 0 433 426 B1, the adjusting mechanism includes a linear slide which is displaceable in two mutually orthogonal directions, and which is arranged in a frame that limits the range of adjustment of the linear slide. This adjusting device is thus comparatively bulky and heavy. Since the equipment is always moved together with the adjusting device, a bulky adjusting device can limit the movement capability of the equipment, and a large mass of the adjusting device can increase the inertia of the movement of the equipment and can make it difficult to balance the stand.

SUMMARY OF THE INVENTION

The object of the invention is to provide a stand according to the concerned category with improved weight equalization.

This object is attained by a stand for a device that is movably arranged, comprising a first stand part having an abutment point, a second stand part that is movable relative to the first stand part, having a pivot arm jointed to the first stand part and pivotably arranged around a pivot axis intersecting the first stand part, and an energy storage device that exerts on a fixed point of action on the pivot arm a force directed to the abutment point on said first stand part, in which the pivot axis and the abutment point define a vertical plane and the abutment point is spatially fixed relative to the first stand part when the pivot arm pivots.

Namely, when with a fixed point of action on the pivot arm the pivot axis and the abutment point define a vertical plane, and the abutment point is spatially fixed relative to the first stand part, the errors inherent in the stands of the prior art due to their finite deflecting roller diameter are eliminated, and a virtually exact weight equalization is thus possible.

In an advantageous manner, the energy storage device includes a compression spring connected as a tension spring. In this manner, a breakage of the energy storage spring cannot lead to an uncontrolled downward motion of the pivot arm.

In a further advantageous embodiment, the energy storage device acts on the pivot arm via a cord linked to the point of action, wherein a cord roller which deflects the cord to the point of action is mounted pivotably about the abutment point located at the outer circumference of the cord roller. The weight advantage of a cord and the low friction roller deflection of a cord are thereby combined with an abutment point which is to a very good approximation fixed in space, thus giving an exact weight equalization to a very good approximation.

When the energy storage device is received in the first stand portion, the energy storage device is particularly space-saving and is accommodated without detriment to handling or adjustment possibilities of the stand.

In a further embodiment, the energy storage device includes a compression spring which is supported between an annular stop which is fixed relative to the first stand part and a displaceable piston connected to the cord. Suitable compression springs which are in good supply can thus be used for the energy storage device.

When the point of action is arranged on a slider, which is displaceable in a longitudinal groove of the pivot arm intersecting the pivot axis orthogonally, the weight equalization can be restored by a simple displacement of the slider, even when there is a weight change of the equipment to be carried by the stand. For this purpose, it is particularly advantageous to permit the slider to engage in a spiral groove which is rotatable around a rotation axis which is orthogonal to the pivot axis. By rotation of the spiral groove, the slider is displaced in its longitudinal groove and the point of action is thereby displaced.

When the spiral groove is constructed as an Archimedean spiral, the displacement of the point of action is always proportional to the rotation angle through which the spiral groove is turned.

In a further, very robust embodiment, the energy storage device acts on the point of action via a pull rod.

When the energy storage device includes a cylinder and piston arrangement, which is rotatably jointed to the first stand part about a rotation axis which contains the abutment point, the fixed position relative to the first stand part is effected precisely and substantially without play.

In relation to the large selection of available compression springs, a compression spring is supported within the cylinder and piston arrangement between a piston connected to the pull rod and an end face of the hollow cylinder.

When the cylinder and piston arrangement is arranged laterally near the pivot arm and the end of the pull rod remote from the piston is jointed to the point of action by means of a transverse rod, the pivoting region of the pivot arm is not restricted by the energy storage device.

According to a further aspect of the invention, the basic object of the invention is also attained by the following features:

A stand comprising a first stand arm, pivotable around a pivot axis, a second stand arm rotatably mounted on the first stand arm around a rotation axis that is parallel to the pivot axis, and a closed cord length that runs around a first deflecting roller that is rotatable around the pivot axis relative to the first stand arm, and a second deflecting roller that is connected non-rotatably with respect to the second stand arm, the closed cord length having at least one rod section between the deflecting rollers.

A stand of the concerned category is thereby provided which has a more exact and directly responsive motion coupling between a first and a second stand arm, and the weight equalization based on this motion coupling is thus improved. The cord extension effects, similar to hysteresis, which are inherent in the state of the art, are substantially eliminated, since according to the invention only the sections of the closed cord length which come directly into contact with the deflecting rollers have to be made of flexible cord.

The very high cord tension in the closed cord is reduced by these features, additionally reducing the cord extension problems, and leading to a reduction of the danger of a cord break and to a reduction of the load on the deflecting rollers.

When the two deflecting rollers have an identical diameter, the motion of the first stand arm relative to a base part of the stand is converted in the same measure to the motion of the second stand arm. When the first deflecting roller is fixed relative to the stand base part, the alignment of the second deflecting roller and thus of the second stand arm to the base part itself can thereby remain unchanged even when the first stand arm pivots.

In an advantageous embodiment, the length of the flexible cord section located between the stiff rod sections limits the pivoting region of the stand arms. The flexible cord sections which are responsible for the residual cord extension effects is kept as short as possible by these means.

In a particularly simple manner, the prestressing of the flexible cord sections cart be adjusted when a rod section is connected to a flexible cord section by means of a coaxial threaded connection. When the rod section has such a threaded connection at both ends and the two threaded connections have an opposite thread sense, the closed cord length can be tensioned by a simple rotation of the corresponding rod section.

According to a further viewpoint of the invention, the object of the invention is also attained by the following features:

A stand for a movably suspended device, comprising a mounting arm, and an adjusting device on the mounting arm, the device being arranged and adjusted on the adjusting device relative to the mounting arm, the adjustment device comprising a linear slide and pivot unit Then by construction of the adjustment device as a linear slide and pivot unit, the adjustment device can be made more compact, i.e. without a frame which limits the adjustment range, and the whole stand can be made lighter, so that its balancing and thus the weight equalization are facilitated.

In an advantageous manner, the linear slide and pivot unit can have a base part, a linear slide displaceable on the base part by means of a screw spindle, and a pivot element which is pivotable relative to the linear slide about a pivot axis, and to which the equipment can be attached.

In an advantageous embodiment, the rotation axis of the screw spindle is then orthogonal to the pivot axis of the pivot element and intersects the pivot element. The adjustment kinematics of the linear slide and pivot unit are thereby particularly clear to the user of the stand.

With the linear slide and pivot unit, the center of gravity of the equipment can be brought particularly quickly and accurately into a rotation axis of the stand, when the linear slide and pivot unit is arranged on the mounting arm, rotatably around this rotation axis, and the pivot axis is parallel to this rotation axis.

In a further advantageous embodiment, the pivot element is pivotable by means of a worm gear, so that the user can manually actuate this worm gear by means of a rotary knob. The user of the stand can then trace, through the torque which the equipment attached to the pivot element produces directly at the rotary knob, the direction in which the pivot element is to be pivoted in the direction of weight equalization or balancing.

According to a further aspect of the invention, the object of the invention is also attained by the following features:

A stand for a movably arranged device, comprising a first stand part, a second stand part that is movable relative to the first stand part and has a pivot arm jointed to the first stand part and pivotable around a pivot axis intersecting the first stand part, in which a torque corresponding to a weight load arranged on the pivot arm at a load distance from the pivot axis acts on the pivot arm, and an energy storage device for equalization of the weight load, comprising a weight equalizing spring with a spring constant that exerts a weight equalizing force on a point of action on the pivot arm, arranged at a distance from the pivot axis, and a deflecting device of finite deflecting radius arranged at a vertical distance from the pivot axis, in which at least one of the spring constant and the vertical distance is smaller than its respective theoretical weight equalization reference value, whereby $$c \cdot r < (G \cdot l)/L,$$

to minimize, in a wide pivoting range of the pivot arm, weight equalization errors caused by the finite deflecting radius.

The weight equalization errors which arise because of the finite deflection radius can be minimized in a wide region of pivoting, by means of the reduction of the spring constant and/or of the vertical distance in relation to their respective theoretical values. Research by the inventors' employer has shown that with suitable values of the spring constant c and vertical distance r, the weight equalization errors can be kept smaller than 1% over a pivoting region of 40°, while the errors with an uncorrected vertical distance r' and an uncorrected spring constant c', in the given pivoting region of 40°, amounted to between minus 4% (torque on the pivot arm is undercompensated) and plus 7% (torque on the pivot arm is overcompensated).

When the weight equalization spring is a compression spring connected as a tension spring, a breakage of the weight equalization spring cannot lead to an uncontrolled downward motion of the pivot arm.

In an embodiment, the deflecting device includes a cord roller, and a cord length running over the cord roller transfers the weight equalizing force from the weight equalization spring to the pivot arm. This embodiment combines the measures for the correction of weight equalization errors with a particularly low friction deflecting device.

When the cord between the weight equalization spring and the cord roller includes a vertical cord section, and the vertical tangent to the cord roller defined by the vertical cord section intersects the pivot axis, the deflecting roller is arranged with respect to the pivot axis and with respect to the direction of the weight equalizing force in a manner which makes the error correction by reduction of the spring constant and/or of the vertical distance particularly effective.

Here the pivot arm can also be pivoted beyond the vertical orientation in two directions when the deflecting device includes a further cord roller arranged at the same vertical distance r from the pivot axis.

Experiments by the inventors' employer have shown that a particularly favorable error correction can be achieved with a difference, which is proportional to the radius of the cord roller, between the vertical distance r and its uncorrected value r'.

It has been found to be particularly favorable for the difference between the vertical distance r and its uncorrected value r' to be 0.35–0.45 times, preferably 0.40 times, the radius of the cord roller, and for the spring constant c to be 0.75–0.85 times, preferably 0.8 times, the uncorrected spring constant c'.

The stands described hereinbelow are in their totality advantageous embodiments of the invention from the aspect of weight equalization. The cooperation of the energy storage arrangement with the rest of the components, in particular equalizing weights, joint parallelograms, cord parallelograms, the linear slide and pivot unit, and the like, of this stand is a particularly advantageous aspect of the invention.

BRIEF DESCRIPTION OF THE DRAWINGS

The invention is described hereinbelow with reference to the accompanying drawings, in which.

DETAILED DESCRIPTION OF PREFERRED EMBODIMENTS

Figure 1:
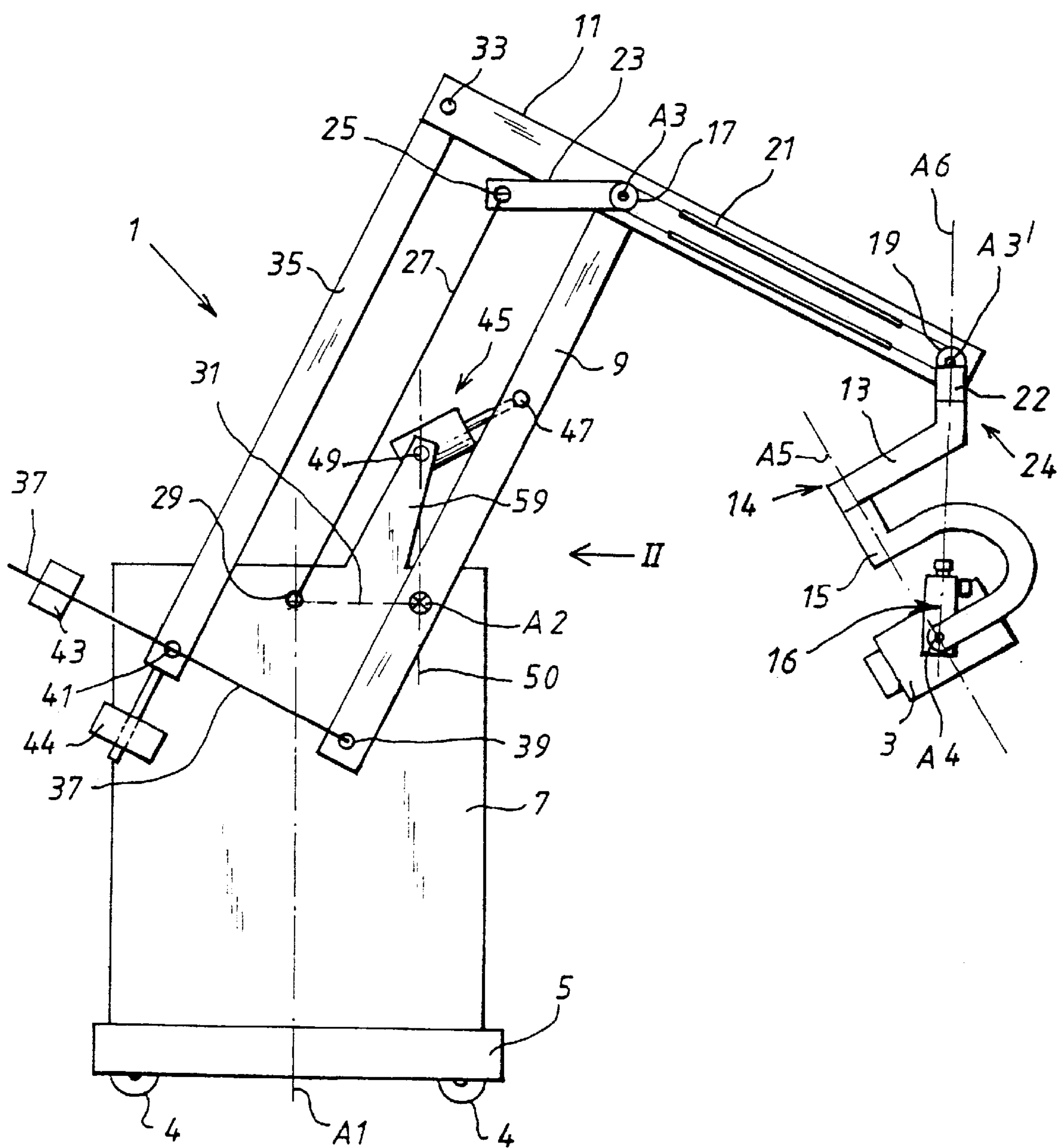
FIG. 1 shows a schematic side view of a stand according to the invention.

FIG. 1 schematically represents an embodiment of the stand according to the invention, in a side view. The stand denoted 1 carries an operation microscope 3 as the equipment, which is to be freely movable.

The stand 1 includes a base part 7 which is rotatable about a vertical rotation axis A1 and is mounted on a foot part 5 which is displaceable by means of rollers 4. A pivot arm 9 is mounted on the base part 7, and is pivotable about a pivot axis A2 which runs orthogonal to the plane of the drawing of FIG. 1.

A carrier arm 11 is jointed to the upper end of the pivot arm 9, and is pivotable relative to the pivot arm 9 around a rotation axis A3 parallel to the pivot axis A2. A connecting piece 22 is jointed to the equipment-side end of the carrier arm 11 around a rotation axis A3' parallel to the rotation axis A3, in a manner such that the connecting piece 22, as shown hereinafter, always retains its alignment. Furthermore, a uniaxial rotary joint 24 is arranged between the connecting piece 22 and an equipment arm 13, and permits the equipment arm 13 to be rotatable around a rotation axis A6.

A mounting arm 15 is jointed to the equipment-side end of the equipment arm 13, and is pivotable around a rotation axis A5. The rotation axis A5 is located in the plane of the drawing of FIG. 1, and must in general not intersect the always vertical rotation axis A6. The equipment arm 13 has an angled shape in order to save space, and has a rotary joint 14 at its end toward the mounting arm and making it possible to rotate the mounting arm 15 around the rotation axis A5.

The operation microscope 3 is installed on the equipment-side end of the mounting arm 15 by means of an adjusting device 16, and is pivotable around the rotation axis A4. The rotation axis runs, in the position of the stand according to FIG. 1, orthogonal to the plane of the drawing of FIG. 1, the mounting arm being constructed such that the rotation axes A4 and A5 intersect orthogonally.

That the operation microscope is freely movable means that inertial moments and/or bearing friction have to be overcome, if need be, but not weight forces or weight torques; i.e., the stand must be in neutral equilibrium with respect to each of its rotary or pivot axes. This is fulfilled when the center of gravity of the masses to be pivoted is located on the respective pivot axis, i.e., when the stand is balanced around this pivot axis.

When the mass center of gravity is not located on the pivot axis, as an alternative an energy storage device can be provided which stores or releases the gravitational energy which is released or supplied by a change of the height position of the moving mass in the Earth's gravitational field, and thereby equalizes the torque of the center of gravity around the pivot axis.

The stand 1 makes use of both possibilities, as is described hereinbelow, with a respective energy storage device associated with the pivot axis A2 and the pivot axis A5, where the stand is to be balanced around the rotation axes A3 and A4. For the rotation axes A1 and A6, it is not necessary to place the center of gravity of the respective moving masses in the rotation axis itself, since gravitational energy is neither released nor expended for a rotation around rotation axes A1 and A6, which are always aligned vertically.

Weight equalization of the stand 1 around the rotation axis A3 will be described first.

A parallelogram arm 35 which is parallel to the pivot arm 9 is jointed to the end of the carrier arm 11 remote from the equipment, by means of a uniaxial rotary joint 33. Furthermore, a connecting rod 37 is jointed by a uniaxial rotary joint 39 to the end of the pivot arm 9 remote from the carrier arm, and by a uniaxial rotary joint 41 to the end of the parallelogram arm 45 remote from the carrier arm. The rotation axes of the joints 33, 39 and 41 are thereby parallel to the rotation axis A3, and it is the case both that the distance between the rotation axis A3 and the rotation axis of the joint 33 is equal to the distance between the rotation axes 39 and 41, and also that the distance between the rotation axis A3 and the rotation axis of the joint 39 is equal to the distance between the joints 33 and 41. The pivot arm 9, parallelogram arm 35, carrier arm 11 and connecting rod 37 thus form a joint parallelogram.

A respective equalization weight 43 or 44 is displaceably arranged on the respective connecting rod 37 or the parallelogram arm 35, in order to balance the stand with respect to its rotation axis A3.

It is solely necessary for this purpose to dimension or arrange the displaceable balancing weight 43 or 44 such that the joint parallelogram as shown in FIG. 1 is stable and open, i.e., includes a surface different from zero. The stand 1 is then in the desired neutral equilibrium with respect to the rotation axis A3.

When there is a weight change of the operation microscope 3, e.g., because of the addition of an operation microscope accessory, the balance with respect to the rotation axis A3 can be reestablished by a corresponding displacement of the equalizing weights 43 and 44.

The weight equalization of the stand around the pivot axis A2 is explained hereinbelow.

Because of the equalizing weights 43 and 44, and also the further joint parallelogram, the masses of the operation microscope 3, mounting arm 15, equipment arm 13 and carrier arm 11 act with respect to the pivot axis A2 and the pivot arm 9 as if a reduced "effective mass" were located on the pivot arm 9 or on an extension of the pivot arm 9.

The energy storage device 45 is provided for equalizing the residual torques exerted by the reduced "effective mass" on the pivot arm 9 around the pivot axis A2, i.e., for weight equalization around the pivot axis A2. The energy storage device 45 is jointed at 47 to the pivot arm 9, and at 49 to the base part 7 of the stand 1. The energy which is released, or has to be supplied, due to the change of the height position of the "effective mass" in the gravitational field of the Earth, when the pivot arm 9 is pivoted around the pivot axis A2, is stored or supplied by the energy storage device 45.

Thus the mass of the equalizing weights 43 and 44 can be kept relatively small by means of the energy storage device 45, or further equalizing weights can be dispensed with, since the equalizing weights 43 and 44 have to produce the neutral equilibrium only with respect to the rotation axis A3, and since favorable lever relationships are present for this purpose due to the relatively large distance of the equalizing weights 43 and 44 from the rotation axis A3. Thus because of the energy storage device 45, the inertial forces to be overcome when the operation microscope 3 is relocated can be relatively small.

The principal manner in which an energy storage device of this kind functions is explained in the article by H. Hilpert in FEINGERÄTETECHNIK, 14th year, Vol. 2/1965, entitled "Weight Equalization in Precision Mechanical Equipment". The energy storage device arrangements shown in FIGS. 6 and 7 of this article are of particular interest in connection with the stand according to the invention.

The energy storage device 45 exerts at 47 on the pivot arm 9 a force which acts in the direction toward the abutment point 49 and which opposes the torque exerted by the "effective mass" on the pivot arm 9 around the pivot axis A2, in order to keep the pivot arm 9 and thus the whole stand in a neutral equilibrium with respect to the pivot axis A2.

By means of such a neutral equilibrium, the operation microscope 3 can be positioned, free from forces, at any position of the working space accessible by movement around the pivot axis A2. Thus each point of a possible displacement path of the operation microscope 3 is an equilibrium point, at which the resultant force acting on the operation microscope 3 disappears. When the operation microscope 3 is relocated, the inertial forces arising due to the moving masses have to be overcome, if need be.

As is apparent from the already cited article, "Weight Equalization in Precision Mechanical Equipment", it is required for the equalization around the pivot axis A2 that the pivot axis A2 and the abutment point 49 are located vertically above or below each other, i.e., a vertical plane 50 must be defined by the pivot axis A2 and the abutment point 49.

The energy storage devices disclosed in the cited journal article fulfill this vertical plane condition, but only for a single pivoting position of the corresponding pivot arm, and the abutment point in the rest of the pivoting region travels out of the vertical plane and thus leads to a residual torque, which is dependent on the pivoting angle, on the pivot arm. In contrast to this known stand, the abutment point 49 of the stand according to the invention remains spatially fixed with respect to the base part when there is a pivoting of the pivot arm 9, and thus always forms, with the pivot axis A2, the vertical plane 50. The stand according to the invention is thus in exact weight equilibrium in each position of the pivot arm 9.

Figure 2:
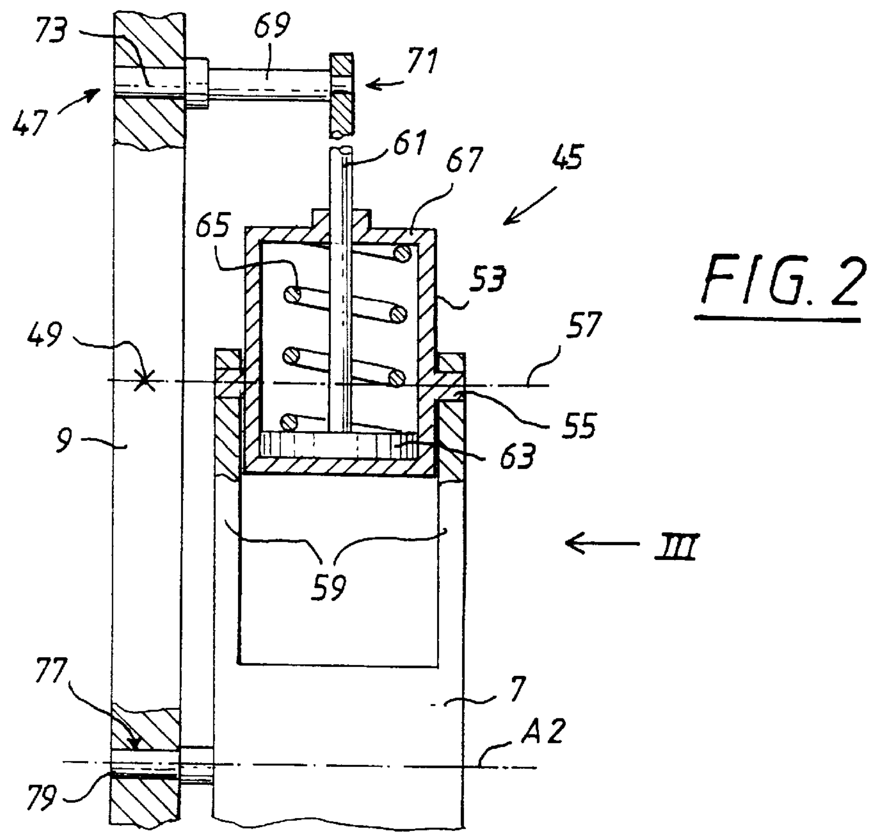
FIG. 2 shows a partially cut-away detail view of the stand, seen in the direction of the arrow II of FIG. 1.

FIG. 2 shows a detail view, partially cut away, of the energy storage device 45, seen in the direction of the arrow II of FIG. 1. in a position of the stand 1 with the pivot arm 9 vertical.

The energy storage device 45 includes a cylindrical housing 53 which is arranged to be rotatable around a rotation axis 57 parallel to the pivot axis A2. For this purpose, two axial pins 55 engage in attachment flanges 59 which are connected fast to the stand base part 7. A pull rod 61 projects into the cylindrical housing 53, and has an end 63 formed as a piston on which the end of a compression spring 65 is supported. The compression spring 65 is supported at its other end, remote from the piston, on the end face 67 of the cylindrical housing 53.

Outside the cylindrical housing 53, the pull rod 61 is connected to a transverse rod 69. The transverse rod 69 is jointed to the pull rod 61 by means of a rotary bearing 71 and to the pivot arm 9 by means of a rotary bearing 73, or the joint 47 shown only schematically in FIG. 1. The abutment point 49 is thus located in the intersection point of the rotation axis 57 of the energy storage device housing 53 with the plane of the joint parallelogram which includes the pivot arm 9 and the parallelogram arm 35.

Furthermore, there can be seen in FIG. 2 a pivot bearing 77 by means of which the pivot arm 9 is mounted on an axial pin 79 of the stand base part, pivotably around the pivot axis A2.

Figure 3:
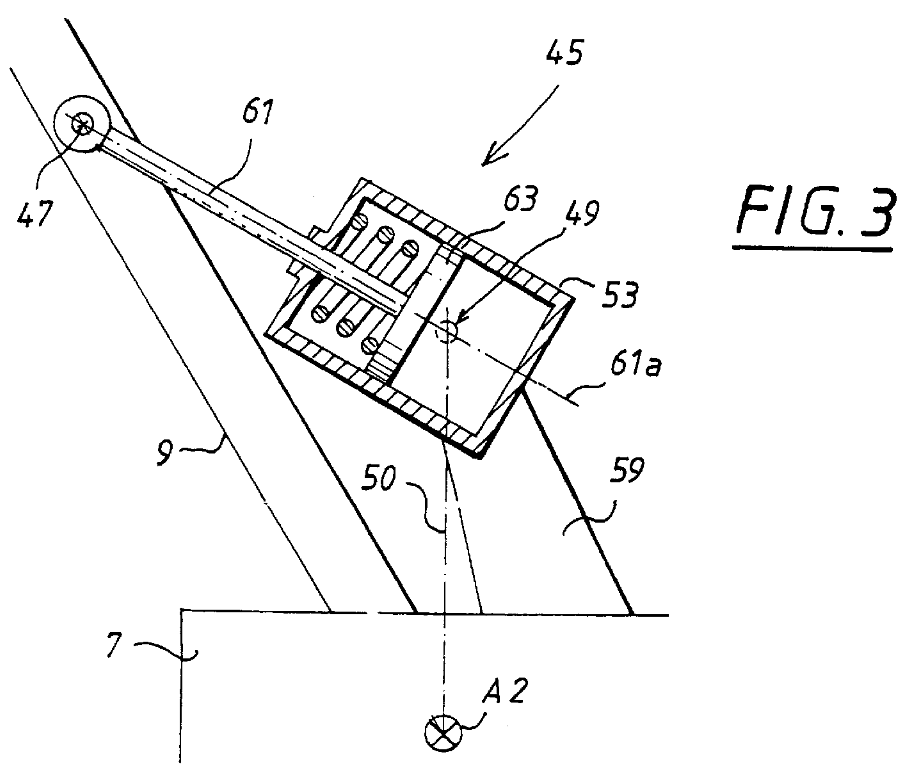
FIG. 3 shows a partially cut-away detail view of the stand, seen in the direction of the arrow III of FIG. 2.

The operation of the energy storage device 45 can be seen from FIG. 3. FIG. 3 is a side view of the detail illustration of FIG. 2 in the direction of the arrow III of FIG. 2, the energy storage device 45 being shown in section. The situation shown in FIG. 3 however differs from FIG. 2 in that the pivot arm is vertically aligned in FIG. 2, and is pivoted in FIG. 3 out of its vertical position into an inclined position.

In the position of the pivot arm 9 shown in FIG. 2, no torque is acting on the pivot arm 9, since the center of gravity of the "effective mass" which loads the pivot arm 9 is exactly vertically above the pivot axis A2. The compression spring, in the stand position according to FIG. 2, therefore takes up the whole space within the energy storage device housing 53.

In the position of the pivot arm 9 shown in FIG. 3, the "effective mass" leads to a torque which tends to rotate the pivot arm 9 around the pivot axis A2. In this position according to FIG. 3, however, the pull rod 61, in contrast to its position according to FIG. 2, is pulled out of the energy storage device housing 53, compressing the compression spring 65. The spring force produced by the compression of the compression spring 65 thus opposes the torque of the "effective mass", and keeps the pivot arm 9 in equilibrium.

The spring force acts in the region of the joint 47 to the pivot arm 9, and is directed toward the abutment point 49, which is located on the rotation axis 57 of the energy storage device housing 53, since the longitudinal axis 61*a* of the pull rod 61 intersects the rotation axis, and the direction of the spring force exerted on the pivot arm 9 is parallel to the pull rod longitudinal axis 61*a*. Here, because of the force transmission by means of the transverse rod 69 shown in FIG. 1, the connecting line between the force action point in the region of the joint 47 and the abutment point 49 is parallel to the pull rod 61.

Since the abutment point 49 is located on the rotation axis 57 of the energy storage device housing 53, and the rotation axis 57 remains spatially fixed during a pivoting motion of the pivot arm 9 around the rotation axis A2, the plane 50, shown dashed in FIGS. 1 and 3, containing the abutment point 49 and the pivot axis A2, is always vertical. The spring constant of the compression spring 65 can be suited to the special stand configuration for each given case of application, and in particular to the specifically selected force action point 47 on the pivot arm 9, from the said article by H. Hilpert See in this connection particularly the equations (15) and (22) on pages 62 and 63 in the said article.

Figures 4, 4A, 4B:
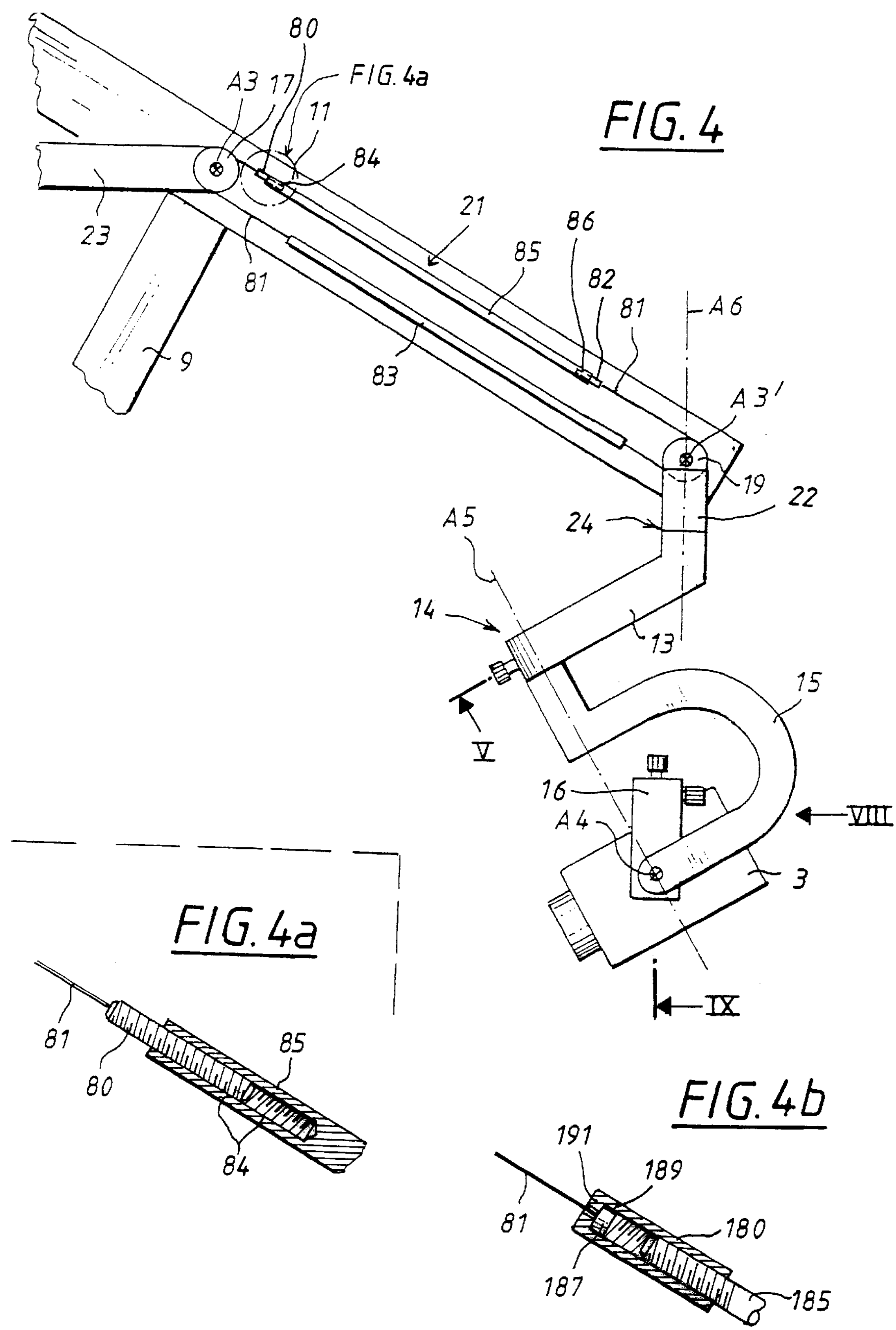
FIG. 4 shows a detail view, corresponding to FIG. 1, of the equipment side stand section.
FIG. 4*a* shows a detail view of FIG. 4.
FIG. 4*b* shows a detail view, corresponding to FIG. 4*a*, of a modification of embodiment shown in FIG. 4*a;*

A further energy storage device 95, shown in FIG. 4, is arranged in the equipment arm 13, and is provided for weight equalization around the rotation axis A5, likewise operating according to the principle laid down in the article by H. Hilpert, and likewise avoids the disadvantages of the energy storage device described in this article.

The structure and manner of operation of this further energy storage device 95, an adjusting element 97 of which can be seen in FIG. 4, will be explained with reference to FIGS. 5, 6 and 7.

Figure 5:
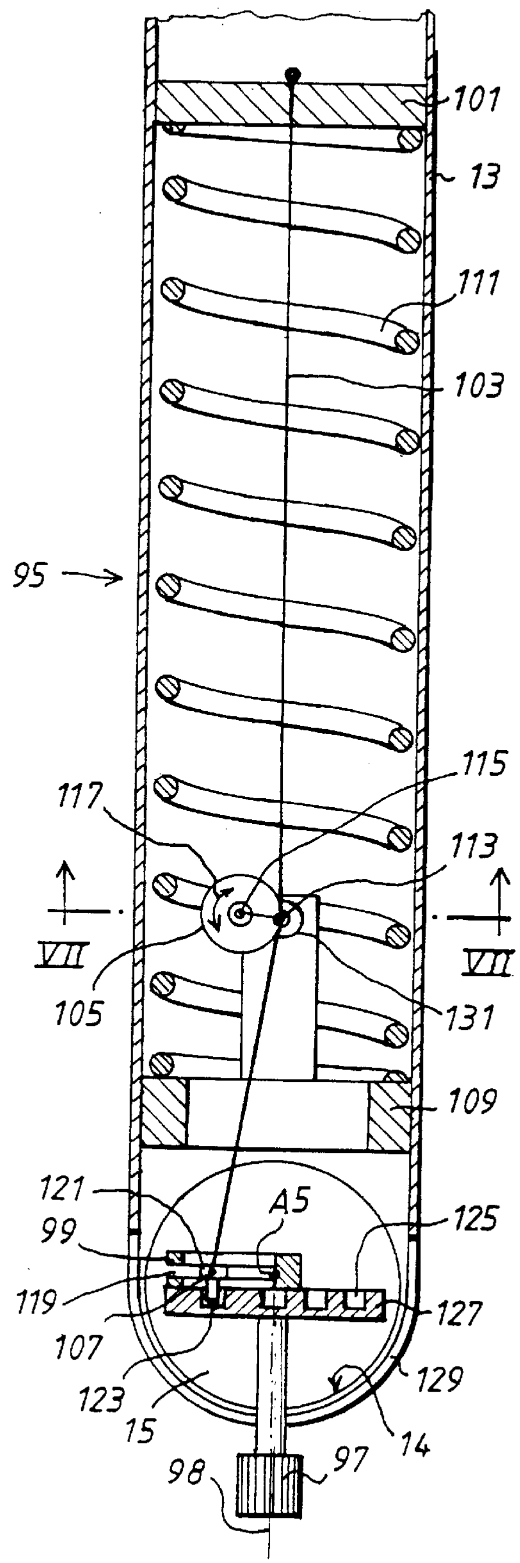
FIG. 5 shows a sectional diagram, seen in the direction of the arrow V of FIG. 4, showing an energy storage device of the stand.

FIG. 5 shows a sectional view, seen in the direction of the arrow V of FIG. 4, of a portion of an energy storage device 95 arranged in the equipment arm 13. Therefore the rotation axis A5 is orthogonal relative to the plane of the drawing of FIG. 5.

Figure 6:
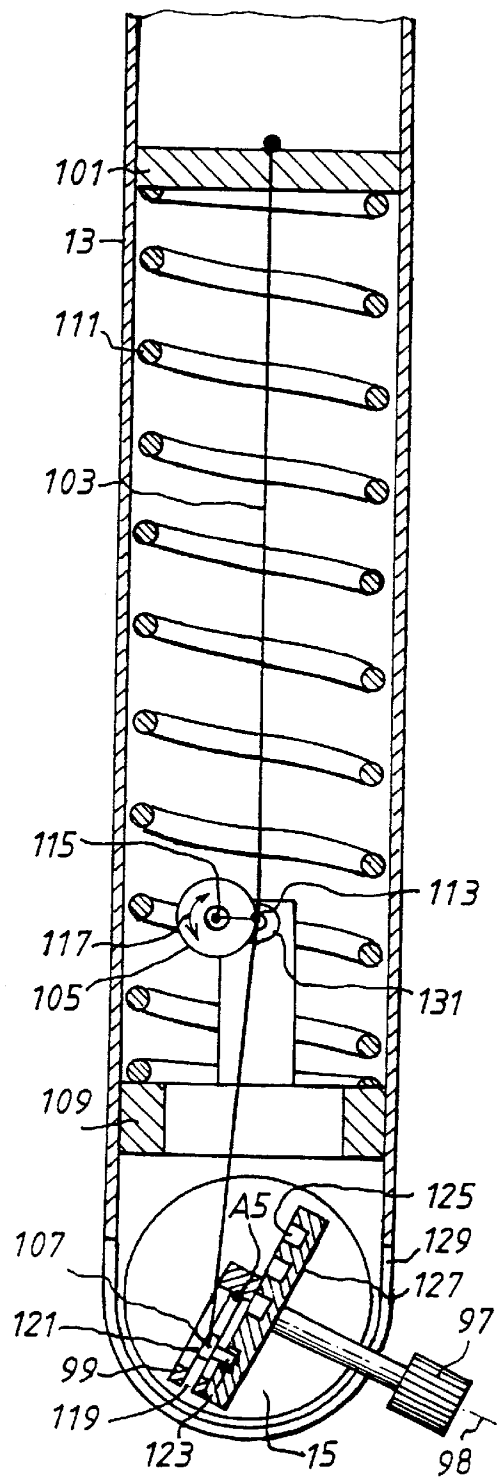
FIG. 6 shows a sectional diagram corresponding to FIG. 5, showing the energy storage device of FIG. 5 in another position of the stand.

FIG. 6 is a sectional diagram corresponding to FIG. 5, and shows the energy storage device 95 in another rotational position of the mounting arm 15 around the rotation axis A5.

A lever arm 99 arranged parallel to the rotation axis A4 is connected fast to the mounting arm 15, and is therefore pivotable together with the mounting arm 15 around the rotation axis A5, the lever arm 99 being orthogonal to, and intersecting, the rotation axis A5.

Since, as explained hereinbelow, the center of gravity of the operation microscope 3 is located on the rotation axis A4, and the rotation axes A4 and A5 intersect orthogonally, the torque exerted by the operation microscope 3 on the mounting arm 15 acts as if the operation microscope 3 were arranged on the lever arm 99 or on an extension of the lever arm 99, where the distance between the intersection point of the rotation axes A4 and A5 and the center of gravity of the operation microscope 3 is to be equated with the lever length l from the said article by H. Hilpert.

The stand 1 can therefore be balanced, with respect to the torque which is exerted around the rotation axis A5 by the operation microscope 3, by means of the energy storage device 95 acting on the lever arm 99.

For this purpose, a cord 103 is tensioned between the lever arm 99 and a piston 101 displaceably received within the cylindrical equipment arm 13; the cord is deflected out of the longitudinal axis of the equipment arm 13, to a point of action 107 on the lever arm 99, by a cord roller 105. A helical compression spring 111 is supported within the equipment arm 13, between the piston 101 and an annular stop 109 on the mounting arm side.

When there is a pivoting of the mounting arm 15 around the rotation axis A5, the compression spring 111 is compressed into the position according to FIG. 6, since the piston 101 is pulled by the cord toward the rotation axis A5 by the rotation, coupled to the pivoting of the mounting arm 15, of the lever arm 99 around the rotation axis A5, and thus the spring force exerted on the mounting arm 15 acts at the point of action 107 and is directed to an abutment point 113 on the periphery of the cord roller 105. This spring force is to compensate the torque exerted on the mounting arm 15 around the rotation axis A5 by the masses of the mounting arm 15, the adjustment device 16 and the operation microscope 3, and to produce a neutral equilibrium with respect to rotation around the rotation axis A5.

The cord roller 105 is mounted in a rocking manner such that it can rotate freely around the abutment point 113; the position change of the midpoint 115 of the cord roller 105 which accompanies a pivoting of the mounting arm 15 is indicated by a double arrow 117. The abutment point 113 thereby remains spatially fixed, even with a pivoting of the mounting arm 15 or of the lever arm 99 around the rotation axis A5.

Since the plane of the drawing of FIG. 4 is a vertical plane, and contains both the rotation axis A5 and the longitudinal axis of the equipment arm 13, and the abutment point 113 is arranged on this longitudinal axis of the equipment arm 13, the abutment point 113, together with the rotation axis A5 of the mounting arm 15, defines a vertical plane. The longitudinal axis of the mounting arm is established in FIG. 4 by the line joining the arrow points of the two arrows V.

Because of the rocker-like mounting of the cord roller 105 at the abutment point 113, as has been explained, it is insured that when there is a pivoting of the mounting arm 15, the midpoint 115 of the cord roller 105 is deflected in a manner such that the abutment point 113 remains spatially fixed, and the plane defined by the rotation axis A5 is always a vertical plane.

Thus, as has already been described in connection with the energy storage device 45 and the pivot arm 9, the mounting arm 15 is in a neutral equilibrium in each of its pivoting positions, provided that the center of gravity of the masses of the mounting arm, the displacement device 16 and the operation microscope 3 is located on the rotation axis A4 parallel to the lever arm 99.

In order to maintain an equilibrium around the rotation axis A5 even when additional components are added to the operation microscope 3, the point of action 107 of the cord 103 is displaceable along the lever arm 99. The energy storage device arrangement shown in principle in FIG. 7 of the article by H. Hilpert is thus reduced to practice.

For this purpose, the point of action 107 is arranged on a slider 121, which is displaceably guided in a longitudinal groove 119, orthogonal to the rotation axis A5, of the lever arm 99. The slider 121 engages with a pin 123 in a spiral groove 125 of an Archimedean spiral 127 which is pivotable with the lever arm 99 around the rotation axis A5. The Archimedean spiral is located in a plane which is parallel to the lever arm 99 and to the rotation axis A5. The Archimedean spiral can be rotated relative to the lever arm 99 around a rotation axis 98, which intersects the rotation axis A5 orthogonally, by means of the rotary knob 97 which is fast to the Archimedean spiral 127, and the distance from the pivot axis A5 of the spring force point of action 107 guided along the lever arm 99 can thus be adjusted. Since the guide groove 125 in which the pin 123 engages is an Archimedean spiral, the change of distance is always proportional to the rotation angle of the rotary knob 97.

Instead of the Archimedean spiral 127 or 125, the slider 121 can however also be adjusted by means of a screw spindle which would be arranged parallel to the rotation axis 99, and would be adjustable by the rotary knob 97 by means of a bevel gear. The rotary knob 97 should be arranged as shown in FIG. 5 relative to the lever arm 99, in order not to limit the pivoting region of the mounting arm 15 by stops at the ends of the slot 129 in the equipment arm 13.

Figure 7:
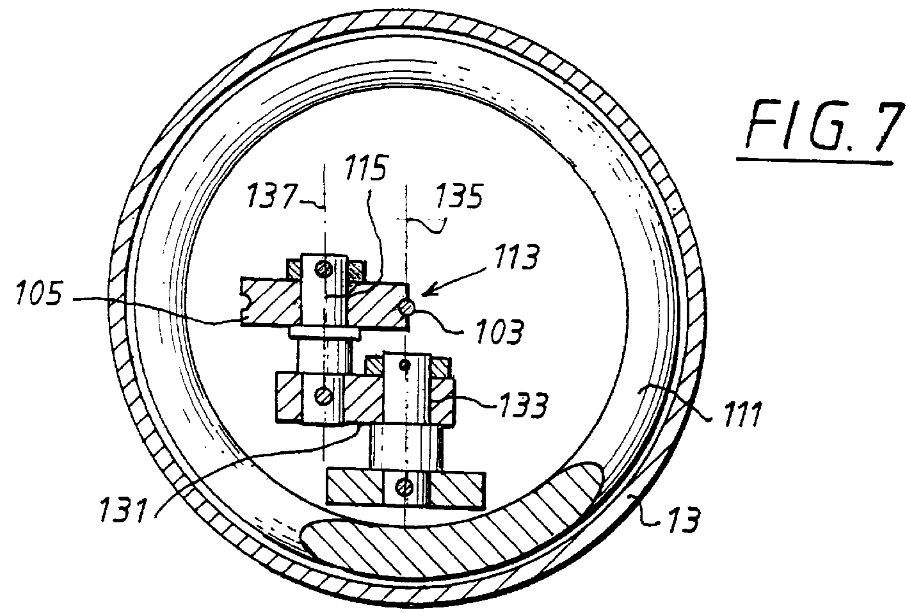
FIG. 7 shows a sectional diagram of the energy storage device along the line VII—VII of FIG. 5.

The rocker-like mounting of the cord roller 105 is shown in detail in FIG. 7, which is a sectional view seen in the direction of the arrows VII of FIG. 5.

The cord roller 105 is mounted on a carrier part 131, and is rotatable around a rotation axis 137 which passes through its midpoint 115. The carrier part 131 is mounted on the annular stop 109 of the equipment arm 13, and is rotatable, by means of a rotary bearing 133, around a rotation axis 135 which intersects the abutment point 113. The cord roller 105 is thus mounted, rotatable around the rotation axis 135, in a rocker-like manner in the abutment point 113, the abutment point 113 being arranged in the middle of the finite cross section of the cord 103 and on the rotation axis 135.

For the energy storage device 95 also, the suitable spring constant of the compression spring 111, and the position of the force point of action 107 on the lever arm 99, for each given case of application, can be directly determined from the said article by H. Hilpert; see in particular Equations (15) and (22) on pages 62 and 63 of this article. The energy storage device 95 here offers the possibility of producing the respective weight equalization, at a suitably chosen middle spring constant, by trial, i.e., by suitable displacement of the force point of action 107.

Returning to FIG. 1, it is explained hereinbelow why the rotation axis A6 is always vertically aligned, and thus an energy storage device associated with the rotation axis A6, or an adjustment/displacement of the center of gravity of the masses which pivot about the rotation axis A6, can be dispensed with.

A deflecting roller 17 which is fast to a horizontal arm 23, which is always horizontally directed, is mounted at the upper end of the pivot arm 9, centrally with respect to the rotation axis A3. A further deflecting roller 19, rotatable relative to the carrier arm 11, is mounted centrally around a rotation axis A3' parallel to the rotation axis A3, at the end of the carrier arm 11 on the equipment arm side. Thus a closed cord length 21 runs without slip around the deflecting rollers 17 and 19. The connecting piece 22 is arranged non-rotatably on the deflecting roller 19.

The horizontal arm 23, arranged non-rotatably on the deflecting roller 17, is connected by means of a uniaxial rotary joint 25 to one end of a parallelogram rod 27, the other end of the parallelogram rod 27 being jointed, by a uniaxial rotary joint 29, to the base part 7 of the stand 1. The rotation axes of the joints 25 and 29 then run parallel to the rotation axis A2 or A3.

The section of the pivot arm 9 located between the rotation axes A2 and A3 forms a joint parallelogram arm, taken together with the parallelogram rod 27 and also the horizontal arm 23 and the imaginary (and therefore shown dashed in FIG. 1) connecting line 31 between the pivot axis A2 and the joint 29. The distance between the pivot axis A2 and the rotation axis A3 is thus equal to the distance between the rotation axis of the rotary joint 25 and the rotation axis of the rotary joint 29. Furthermore, the distance between the pivot axis A2 and the rotation axis of the joint 29 is equal to the distance between the rotation axis A3 and the rotation axis of the joint 25. Since in addition the horizontal position of the connecting line 31 (shown dashed) does not change during a pivoting of the stand 1 around the axes A1–A6, the horizontal arm 23 is always aligned horizontally, independently of the respective position of the pivot arm 9.

With a pivoting of the carrier arm 11 around the rotation axis A3, or with a pivoting of the pivot arm 9 around the pivot axis A2, the deflecting rollers 17 and 19 always rotate relative to the carrier arm 11 such that the orientation of the deflecting rollers 17 and 19 always remains constant, since the horizontal arm is indeed connected fast to the deflecting roller 17, and the deflecting roller is coupled slip-free to the deflecting roller 19 by the closed cord length which forms a cord parallelogram.

Since the equipment arm 13 is connected fast to the deflecting roller via the connecting piece 22, its orientation relative to the vertical direction also always remains constant The rotation axis A6 also itself therefore always remains vertically aligned during a pivoting of the pivot arm 9 or of the carrier arm 11.

The region of the stand 1 which includes the front section of the carrier arm 11, the equipment arm 13, the mounting arm 15 and the operation microscope 3 is shown in FIG. 4.

It can be seen from FIG. 4 that the closed length of cord 21 is constructed as a flexible cord 81 in the region of the deflecting rollers 17 and 19, and as a rigid rod section, 83 or 85, between the rollers 17 and 19. The cord sections 81 engage around the deflecting rollers 17 and 19 without slip, and are dimensioned such that a contact of the rigid rod sections 83 and 85 with the deflecting rollers 17 or 19 is avoided over the whole pivoting range of the carrier arm 11.

By such a design of the deflecting rollers 17 and 19 and also of the cord parallelogram including the closed cord length 21, the weight advantage of a cord parallelogram in comparison with a rod parallelogram can be retained, while the cord extension effects, similar to hysteresis, occasioned by a cord can be substantially minimized. Thus the low weight of a length of cord can be combined with the high rigidity of a rod. A very high cord tension would be required to suppress these extension effects similar to hysteresis if the cord parallelogram rods 83 and 85 were omitted, and would excessively load the bearings of the deflecting rollers 17 and 19.

It can furthermore be seen in FIG. 4, and particularly in the enlarged detail excerpt according to FIG. 4*a*, that the rigid rod section 85 has at each end a respective internal thread 84 and 86. The internal thread 84 is a right-hand thread, and the internal thread 86 is a left-hand thread. Corresponding stud screws 80 and 82, which are firmly connected to the flexible cord sections 81, are screwed into these internal threads 84 and 86. It goes without saying that the pretension of the closed cord length can be changed by rotating the rod section 85.

A further possibility for connecting the rigid rod section to the flexible cord section is shown in FIG. 4*b*.

In this embodiment, the rod section 185 has an external thread which is screwed into a threaded bore 189 of an end piece 180 formed as a sleeve. At its end remote from the rod, the connector 189 has an annular shoulder on which is supported a disk 187 firmly connected to the cord 81.

In this embodiment, the other end of the rod section 185 can be connected to the cord section by means of a like connector or by a clamping element.

The weight equalization of the stand around the rotation axis A4 will be described hereinbelow.

For this purpose, the center of gravity of the operation microscope 3 is brought onto the rotation axis A4 by means of the adjusting device 16 connected between the mounting arm 15 and the operation microscope 3, and thus balances the stand 1 around the rotation axis A4.

Figure 8:
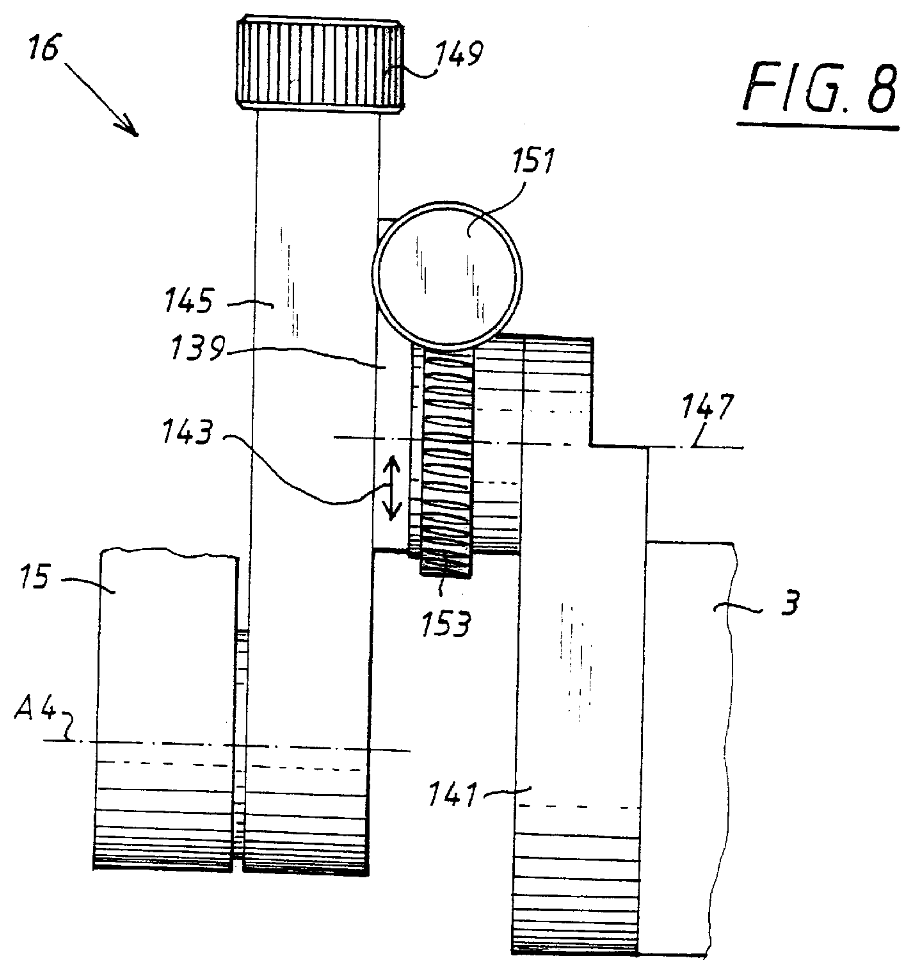
FIG. 8 shows a side view seen in the direction of the arrow VIII of FIG. 4, and showing a linear slide and pivot unit in detail.

FIG. 8 shows the adjusting device 16 in a side view, seen in the direction of the arrow VIII of FIG. 4.

The adjusting device 16 is constructed as a linear slide and pivot unit, which includes a linear slide 139 and a pivot element 141. The linear slide 139 is displaceable in the direction of the double arrow 143 on a base part 145, which can be pivoted around the rotation axis A4, of the linear slide and pivot unit 16. The pivot element 141 is arranged, pivotably around a pivot axis 147, on the linear slide 139 and therefore displaceable with this in the direction of the double arrow 143. The operation microscope 3 is then firmly fixed to the pivot element 141. Since the base part 145 is jointed, rotatably around the rotation axis A4, to the mounting arm 15, the operation microscope 3 together with the linear slide and pivot unit 16 can also be rotated around the rotation axis A4.

Furthermore, a rotary knob 149 for displacing the linear slide 143, and a further rotary knob 151 for pivoting the pivot element 141 around the pivot axis 147, can be seen in FIG. 8. The rotary knob 151 acts for this purpose on a worm wheel 153 with helical gearing, formed on the pivot element 141.

Figure 9:
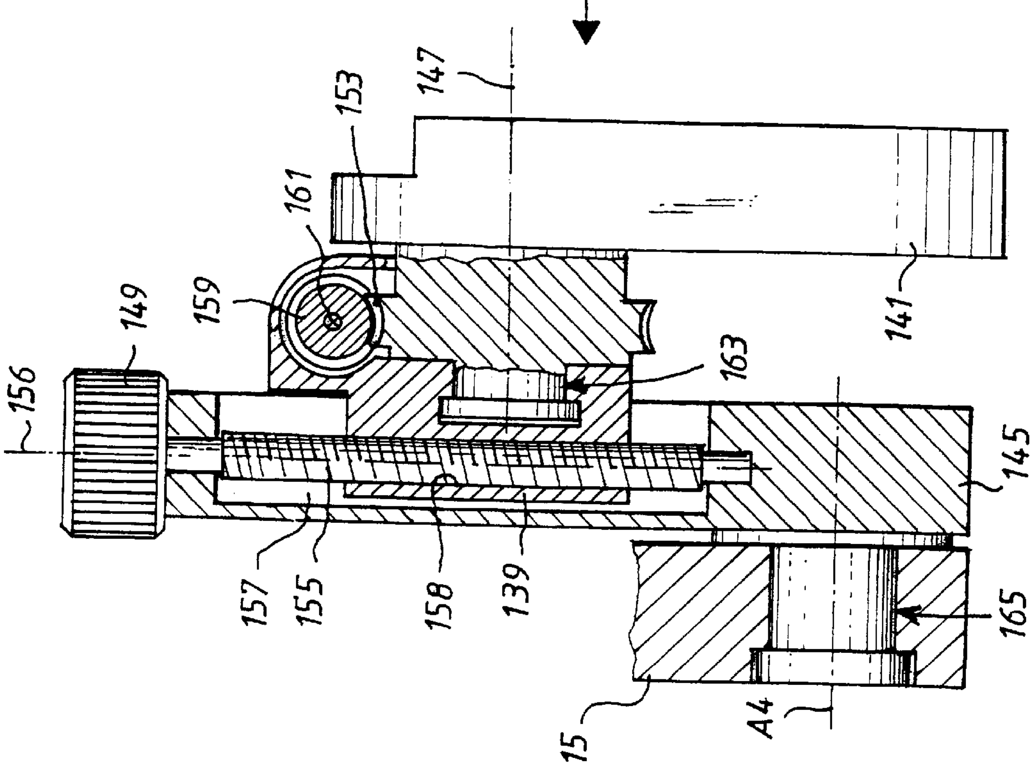
FIG. 9 shows a sectional diagram of the linear slide and pivot unit of FIG. 8 and running along the line IX—IX of FIG. 4.

FIG. 9 shows the linear slide and pivot unit 16 in a sectional view which includes the rotation axes A4 and 147, along the line of section established by the arrow IX in FIG. 4.

It can be seen in FIG. 9 that a screw spindle 155 can be rotated with the rotary knob 149 about a rotation axis 156 in the plane of the drawing of FIG. 9. The screw spindle 155 passes through a threaded bore 158 of the linear slide 139 which is displaceably guided in the recess 157 of the base part 145 in the direction of the double arrow 143 of FIG. 8. By rotating the rotary knob 149, the linear slide 139, and with it the operation microscope 3, can thus be moved upward or downward relative to FIG. 9.

A further screw spindle 159 is arranged on the linear slide 139, and is rotatable around a rotation axis 161 running orthogonally to the plane of the drawing of FIG. 9. The further screw spindle 159 then meshes with the inclined thread of the worm wheel 153 of the pivot element 141. Since the worm wheel 153 is rotatable around the rotation axis 147 relative to the linear slide 139 by means of the rotary bearing 163, the pivot element 141 and thus the operation microscope 3 can be pivoted by a rotation of the screw spindle 159. Such a rotation of the screw spindle is effected by the rotary knob 151 which is connected fast to the screw spindle 159, as may be seen in FIG. 8.

In FIG. 9, the rotation of the linear slide and pivot unit 16 around the rotary bearing 165, which makes possible the rotation axis A4 may furthermore be seen.

Figure 10:
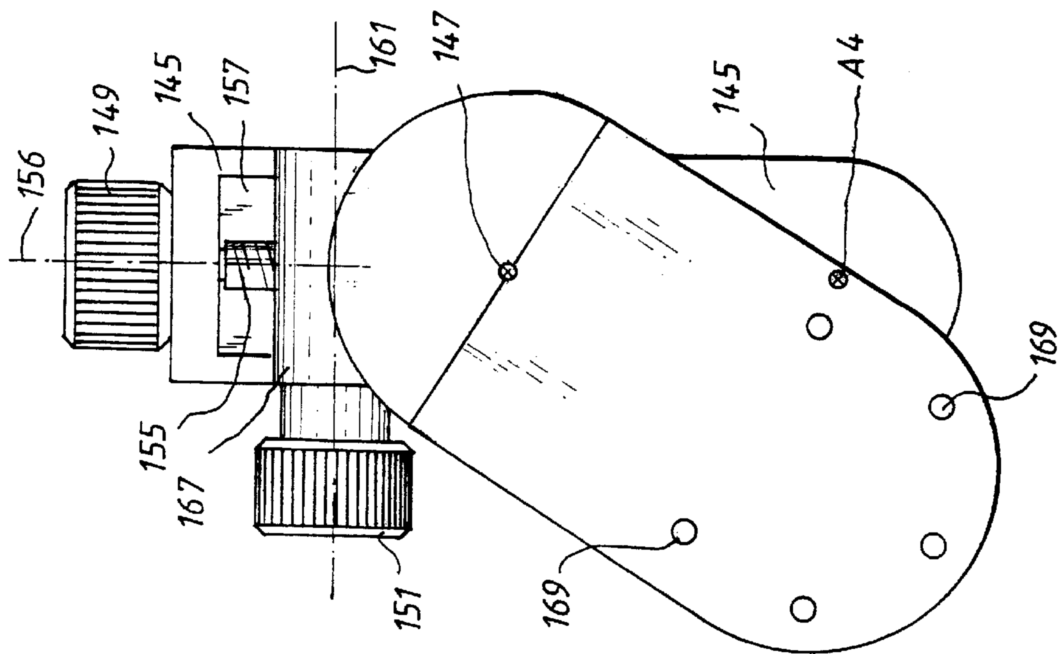
FIG. 10 shows a side view, seen in the direction of the arrow X of FIG. 9, of the linear slide and pivot unit, with a pivot element pivoted out of the vertical.

FIG. 10 is a plan view, seen in the direction X of FIG. 9, of the linear slide and pivot unit 16, with the pivot element 141 pivoted out of the vertical.

In FIG. 10, the section 167 of the linear slide 139 which receives the screw spindle 159 is clearly evident, and fastening holes 169 are to be seen, formed on the pivot element 141; by means of these holes, the operation microscope (not shown in FIG. 10 for reasons of illustration) is attached to the pivot element 141. The rotation axis A4 runs, in exactly the same way as the rotation axis 147, orthogonal to the plane of the drawing of FIG. 10. It is to be noted that only the pivot element 141 is pivotable around the rotation axis 147; however, the whole linear slide and pivot unit 16 shown in FIG. 10 is pivotable around the rotation axis A4.

Figure 11:
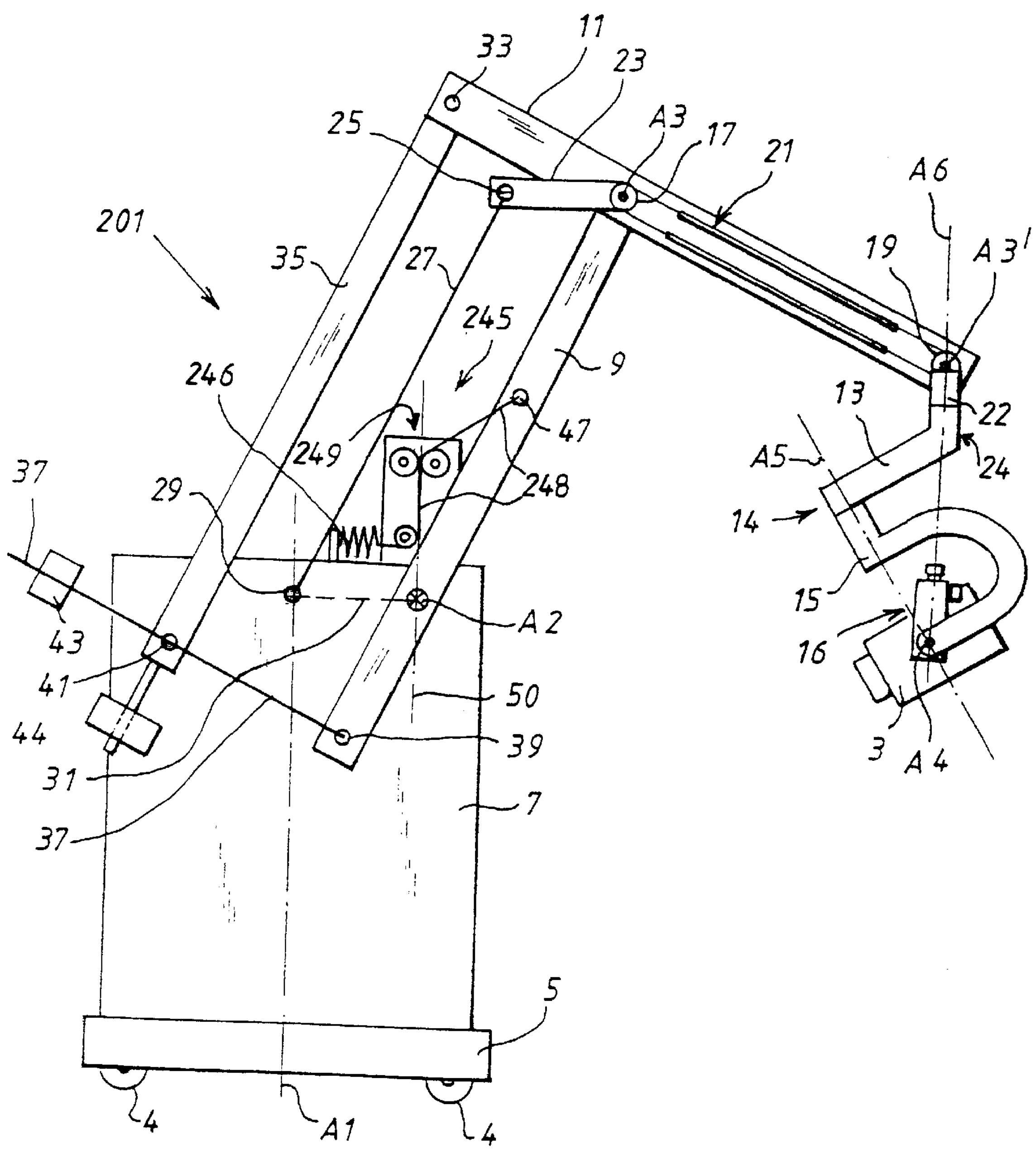
FIG. 11 shows a schematic side view of a further stand according to the invention.

A further stand 201 according to the invention is shown schematically in a side view in FIG. 11. The elements of the stand which correspond to the elements of the stand 1 of FIGS. 1–10 are given the same reference numbers as in FIGS. 1–10, and reference is made to the description of FIGS. 1–10 for their explanation.

The weight equalization of the stand around the pivot axis A2 will be explained hereinbelow.

For the equalization of the residual torque exerted on the pivot arm 9 around the pivot axis A2 by the "effective mass", i.e., for the weight equalization around the pivot axis A2, the energy storage device 245 is provided which acts in a manner analogous to the energy storage device 45.

The energy storage device 245 includes a weight equalization spring 246 which exerts a weight equalizing force on the pivot arm 9 at a point of action 47 by means of a cord length 248. The cord length 248 is deflected out of the vertical plane 50 to the point of action 47 by means of a deflecting device 249.

Figure 12:
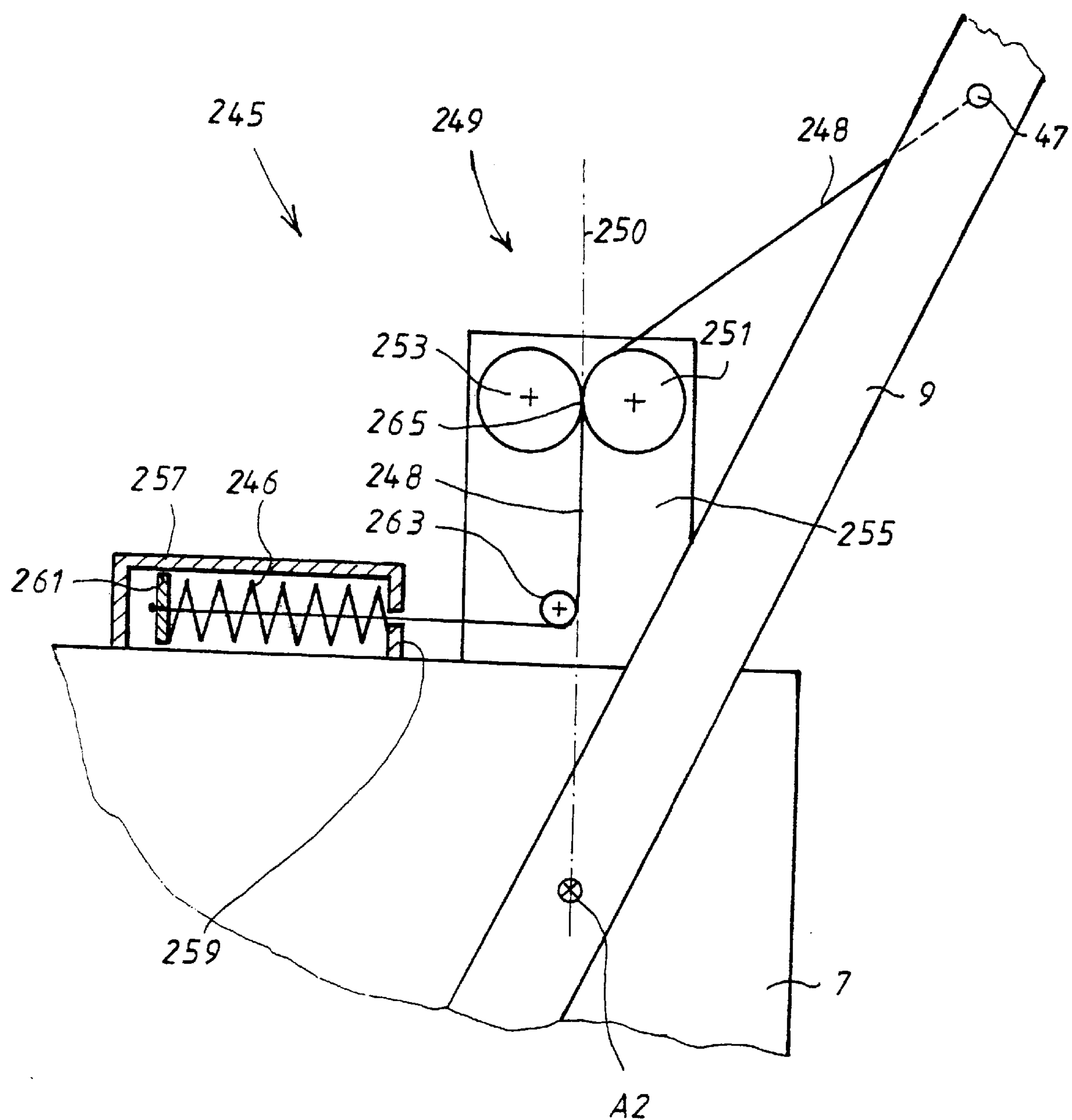
FIG. 12 shows a detail view, corresponding to FIG. 11, of the stand section including the energy storage device.

FIG. 12 shows the energy storage device 245 in detail.

The cord length 248 is coupled to the weight equalizing spring 246. It is to be recognized that the deflecting device 249 which deflects the cord length 248 to the point of action 47 includes a first cord roller 251 and a second cord roller 253 which are arranged on a section 255 of the base part 7 for rotation around rotation axes parallel to the pivot axis A2.

The weight equalizing spring 246 is arranged in a housing 257 and is supported between a housing end wall 259 and a disk 261 which is movable in the housing. The cord length 248 is attached to the disk 261, passes through the end wall 259, and is deflected by a deflecting roller 263 to the cord rollers 251 and 253. Here the section of the cord length 248 runs between the deflecting roller 263 and the point of action 265 of the two cord rollers 251 and 253 in the vertical plane which contains the pivot axis A2.

According to the article by H. Hilpert, the stand is equalized with respect to a weight G acting on the pivot arm at a load distance l from the pivot axis A2, when $$c' \cdot r' \cdot L = G \cdot l,$$

where c' is the spring constant of the weight equalizing spring, r' is the vertical distance of the deflecting device from the pivot axis, and L is the distance of the point of action from the pivot axis.

However, this condition only insures an exact weight equalization when the cord length runs along a straight line between the point of contact 265 and the point of action 47. The finite radius of the cord roller 251 or 253 leads however to the cord length 248 between the point of contact 265 and the point of action 47 includes an arcuate section which runs on the circumference of the cord roller 251 (or the cord roller 253, when the pivot arm 9 is deflected to the left).

In order to be able to attain as exact as possible a weight equalization even though using a deflecting device with a finite deflecting radius, according to the invention the following holds:

$$c \cdot r < (G \cdot l)/L$$

where c is the spring constant of the spring 246 and the vertical distance r is the distance between the point of contact 265 and the pivot axis A2.

These values c and r which are corrected in relation to the finite deflection radius are determined, starting from c' and a predetermined r', such that the difference between r and r' is 0.4 times the radius of the cord roller 251, and the spring constant c is 0.8 times c'.

We claim:

1. A stand (1) for a device (3) that is movably arranged, comprising:

a first stand part (7; 13) having an abutment point (49; 113), a second stand part (9, 11; 15, 16) that is movable relative to said first stand part (7; 13), having a pivot arm (9; 15) jointed to said first stand part (7; 13) and pivotably arranged around a pivot axis (A2; A5), and an energy storage device (45; 95) that exerts on a fixed point of action (47; 107) on said pivot arm (9, 15) a force directed to said abutment point (49; 113) on said first stand part (7; 13), in which said pivot axis (A2; A5) and said abutment point (49; 113) define a vertical plane (50; plane of the drawing in FIG. 4) and said abutment point (49; 113) is spatially fixed relative to said first stand part (7; 13) when said pivot arm (9; 15) pivots.

2. The stand according to claim 1, in which said energy storage device (45; 95) includes a compression spring (65; 111) arranged to provide tension.

3. The stand according to claim 1, in which said energy storage device (95) comprises a cord (103) jointed to said point of action (107) and acting on said second stand part (9, 11; 15, 16), and a cord roller (105) that deflects said cord (103) to said point of action (107) and is mounted to pivot around said abutment point (113), which is located on the external circumference of said cord roller (105).

4. The stand according to claim 3, in which said energy storage device (95) further comprises an annular stop (109) that is fixed relative to said first stand part (13) and a displaceable piston (101) connected to said cord (103) that supports said compression spring (111) between said annular stop (109) and said displaceable piston (101).

5. The stand according to claim 1, in which said energy storage device (95) further comprises a slider (121) that is displaceable in a longitudinal groove (119) orthogonally intersecting said pivot axis (A5), said point of action (107) being arranged on said slider.

6. The stand according to claim 5, in which said slider (121) engages in a spiral groove (125) that is rotatable around a rotation axis (98) orthogonal to said pivot axis (A5).

7. The stand according to claim 6, in which said spiral groove (125) is in the form of an Archimedean spiral.

8. The stand according to claim 1, in which said energy storage device (95) is received in said first stand part (13).

9. The stand according to claim 1, in which said energy storage device (45) further comprises a pull rod (61) jointed to said point of action (47), said energy storage device acting on said second stand part (9; 11) through said pull rod (61).

10. The stand according to claim 9, in which said energy storage device (45) includes a cylinder and piston arrangement (53, 63) that is jointed rotatably to said first stand part (7) around a rotation axis (57) containing said abutment point (49).

11. The stand according to claim 10, in which said energy storage device (45) further comprises a compression spring (65) supported within said cylinder and piston arrangement (53, 63) between a piston (63) connected to said pull rod (61) and an end face (67) of said cylinder (53).

12. The stand according to claim 10, in which said cylinder and piston arrangement (53, 63) is arranged laterally near said pivot arm (9), the end of said pull rod (61) remote from said piston (63) being jointed to said point of action (47) through a transverse rod (69).

13. A stand (1; 201) comprising:

a first stand arm (11), pivotable around a pivot axis (A3), a second stand arm (13) rotatably mounted on said first stand arm (11) around a rotation axis (A3') that is parallel to said pivot axis (A3), and a closed cord length (21) that runs around a first deflecting roller (17) that is rotatable around said pivot axis (A3) relative to said first stand arm (11), and a second deflecting roller (19) that is connected non-rotatably with respect to said second stand arm (13), said closed cord length (21) having at least one rod section (83, 85) between said deflecting rollers (17, 19).

14. The stand according to claim 13, in which the diameter of said first deflecting roller (17) is equal to the diameter of said second deflecting roller (19).

15. The stand according to claim 14, further comprising a stand base part (7), said first deflecting roller (17) being fastened non-rotatably with respect to said stand base part (7).

16. The stand according to claim 13, in which said closed cord length (21) includes two rod sections (83, 85) and a length of cord section (81) located between said two rod sections (83, 85) that limits the pivoting region of said first stand arm (11).

17. The stand according to claim 13, further comprising a cord section (81) of said closed cord length (21) and at least one threaded connection (80, 84) connecting said rod section (85) to said cord section (81).

18. The stand according to claim 17, in which said rod section (85) has said threaded connections (80, 84) at each of its ends, said threaded connections (80, 84) having threads of opposite senses.

19. A stand (1; 201) for a movably suspended device (3), comprising:

a mounting arm (15), and an adjusting device on said mounting arm (15), said movably suspended device (3) being arranged and adjusted on said adjusting device relative to said mounting arm (15), said adjusting device comprising a linear slide pivot unit (139, 141).

20. The stand according to claim 19, in which said linear slide and pivot unit (139, 141) comprises a base part (145), a linear slide (139) displaceable on said base part (145), and a pivot arm (141) pivotably arranged on said linear slide (139) relative to said linear slide (139) around a pivot axis (147), said device (3) being fastened to said pivot arm (141).

21. The stand according to claim 20, in which said slide and pivot unit (139, 141) further comprises a screw spindle (155) arranged to displace said linear slide (139) on said base part (145).

22. The stand according to claim 21, in which the rotation axis (156) of said screw spindle (155) is orthogonal to and intersects said pivot axis (147) of said pivot element (141).

23. The stand according to claim 20, in which said linear slide and pivot unit (139, 141) is rotatably arranged around a rotation axis (A4) on said mounting arm (15), said pivot axis (147) of said pivot element (141) being parallel to said rotation axis (A4).

24. The stand according to claim 20, in which said linear slide and pivot unit (139, 141) further comprises a worm gear (153, 159) that is arranged to pivot said pivot element (141).

25. A stand for a movably arranged device (3), comprising:

a first stand part (7), a second stand part (9, 11, 13, 15) that is movable relative to said first stand part (7) and has a pivot arm (9) jointed to said first stand part (7) and pivotable around a pivot axis (A2), in which a torque corresponding to a weight load (G) arranged on said pivot arm (9) at a load distance (1) from said pivot axis (A2) acts on said pivot arm (9), and an energy storage device (245) for equalization of said weight load (G), comprising a weight equalizing spring (246) with a spring constant (c) that exerts a weight equalizing force on a point of action (47) on said pivot arm (9), arranged at a distance (L) from said pivot axis (A2), and a deflecting device (249) of finite deflecting radius arranged at a vertical distance (r) from said pivot axis (A2), in which at least one of said spring constant (c) and said vertical distance (r) is smaller than its respective theoretical weight equalization reference value, whereby $$c \cdot r < (G \cdot l)/L,$$

to minimize, in a wide pivoting range of said pivot arm (9), weight equalization errors caused by said finite deflecting radius.

26. The stand according to claim 25, in which said weight equalization spring (246) comprises a compression spring arranged to provide tension.

27. The stand according to claim 25, in which said deflecting device (249) comprises a cord roller (251) and a cord length (248) running over said cord roller (251) that transmits said weight equalizing force from said weight equalizing spring to said pivot arm (9).

28. The stand according to claim 27, in which said cord length (248) includes a vertical cord length section between said weight equalization spring (246) and said cord roller (251), a vertical tangent to said cord roller (251) defined by said vertical cord length section intersecting said pivot axis (A2).

29. The stand according to claim 28, in which said deflecting device (249) includes a further cord roller (253) arranged at said vertical distance (r) from said pivot axis (A2).

30. The stand according to claim 25, in which the difference between said vertical distance (r) and the uncorrected theoretical value of said vertical distance (r'), with a predetermined uncorrected spring constant (c') according to the equation $$c' \cdot r' \cdot L = G \cdot l$$

is proportional to the radius of said cord roller (251, 253).

31. The stand according to claim 30, in which the difference between said vertical distance (r) and said uncorrected value (r') is 0.35–0.45 times the radius of said cord roller (251, 253), and said spring constant (c) is 0.75–0.85 times said uncorrected spring constant (c').

32. The stand according to claim 31, in which said uncorrected value (r') is 0.4 times the radius of said cord roller (251, 253).

33. The stand according to claim 31, in which said spring constant (c) is 0.8 times said uncorrected said spring constant (c').

* * * * *